United States Patent [19]

Tsurumi

[11] Patent Number: 5,358,874
[45] Date of Patent: Oct. 25, 1994

[54] NITROGEN OXIDE ANALYZER AND METHOD OF MEASURING OXIDES OF NITROGEN

[75] Inventor: Kazuya Tsurumi, Miyanohigashi, Japan

[73] Assignee: Horiba, Ltd., Kyoto, Japan

[21] Appl. No.: 116,362

[22] Filed: Sep. 3, 1993

[30] Foreign Application Priority Data

Sep. 9, 1992 [JP] Japan .............................. 4-069813[U]

[51] Int. Cl.$^5$ ............................................ G01N 21/76
[52] U.S. Cl. ..................................... 436/116; 436/106; 436/114; 436/117; 436/118; 422/52; 422/83
[58] Field of Search ............. 422/52, 80, 82.05, 82.09, 422/83, 89, 91; 436/52, 53, 106, 107, 110, 114, 115, 116, 117, 118, 172, 179

[56] References Cited

U.S. PATENT DOCUMENTS 3,652,227 3/1972 Harmon, III et al. ............... 436/118
4,863,691 9/1989 Noguchi et al. ...................... 422/54

FOREIGN PATENT DOCUMENTS 0067752 6/1981 Japan .

*Primary Examiner*—David A. Redding
*Attorney, Agent, or Firm*—Poms, Smith, Lande & Rose

[57] ABSTRACT

An NO$_x$ analyzer capable of reducing maintenance operations for removing solid substances from the analyzer, and for obtaining an analytical value of improved reliability for sample gases flowed through the analyzer is provided. A sample gas supply passage on the downstream side of an NO$_x$ convertor is provided with a first capillary therein; a sample gas supply passage between the first capillary and the NO$_x$ convertor is provided with an overflow passage having a second capillary branch connected therewith; a sample gas supply passage on a downstream side of the first capillary is provided with a diluent air supply passage having a third capillary therein and also branch connected with the sample gas supply passage. At least the confluence of the first capillary, the second capillary, and the diluent supply passage with the sample gas supply passage is arranged within a heating zone of the NO$_x$ analyzer.

14 Claims, 1 Drawing Sheet

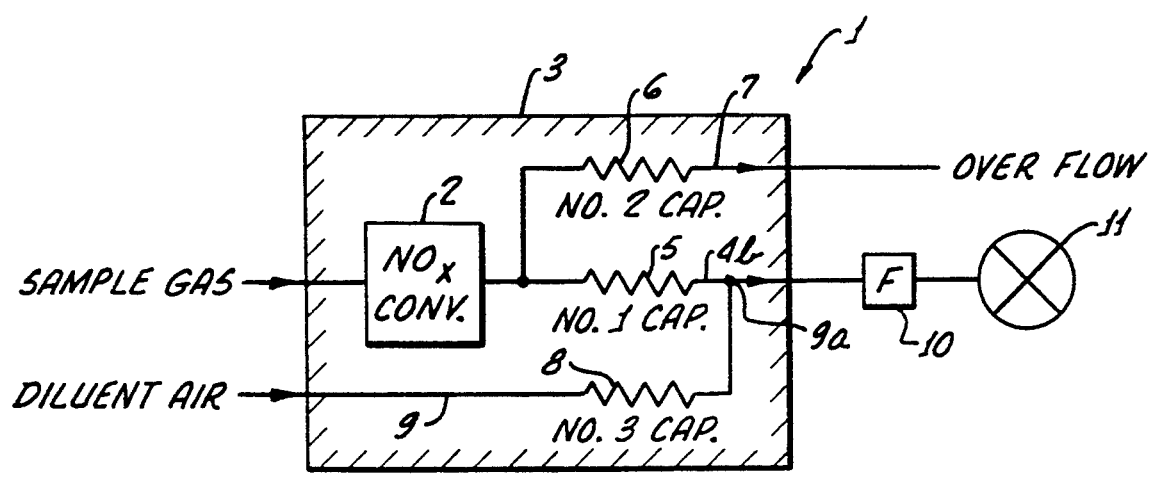

NITROGEN OXIDE ANALYZER AND METHOD OF MEASURING OXIDES OF NITROGEN

BACKGROUND OF THE INVENTION

1. Field of the Invention

The present invention relates to an $NO_x$ analyzer for quantitatively determining nitrogen oxide (hereinafter referred to as $NO_x$) components contained in an exhaust gas from, for example, a diesel engine and the like. In particular, the present invention relates to a chemical luminescence-type $NO_x$ analyzer adapted to introduce a sample gas into an NO detector through an $NO_x$ convertor for reducing $NO_x$ to NO.

2. Description of the Prior Art

In the so-called chemical luminescence-type of $NO_x$ analyzer, NO acts upon ozone to emit a light. The quantity of emitted light has been detected to quantitatively determine $NO_x$ components in a sample gas. The $NO_x$ components in the sample gas are first reduced to NO by means of an $NO_x$ convertor, and then are introduced into a reaction tank for reacting the resulting NO with ozone.

However, in the case where aromatic hydrocarbons, such as xylene, are contained in the sample gas, then when the sample gas is heated to about 220° C. in a heater incorporated in the $NO_x$ convertor, the aromatic hydrocarbons are oxidized to be turned into phthalic acid anhydride. Because phthalic acid anhydride has a high saturated vapor pressure at high temperatures of about 200° C., or more, it exists in the gaseous form at these temperatures. However, the phthalic acid anhydride is apt to sedimentate in the solid form at lower and normal temperatures. Because such solidified phthalic acid anhydride is apt to clog a capillary arranged immediately before the NO detector, and thus to lower the accuracy of measurement provided by the $NO_x$ analyzer, a filter has been arranged in the vicinity of a sample gas exhaust port of the $NO_x$ convertor. That is, conventionally a filter may be installed between the $NO_x$ convertor and the NO detector.

However, in the case where solidified phthalic acid anhydride is removed by such a filter, as above described, difficulties have occurred. These difficulties include, for example, a necessity for frequent maintenance operations to clean, exchange, and to otherwise service the filter. These frequent maintenance operations cause increased idle time and increased operating costs for the $NO_x$ analyzer.

SUMMARY OF THE INVENTION

The present invention has been developed in view of the above-described actual circumstance, and it is an object of the present invention to provide an $NO_x$ analyzer capable of reducing maintenance operations for removing solid substances, such as solidified phthalic acid anhydride, and for thereby obtaining an improved and more reliable analytical value from an $NO_x$ analyzer.

In order to achieve the above-described object, an analyzer adapted to introduce a sample gas into an NO detector through an $NO_x$ convertor and embodying the present invention comprises: an $NO_x$ convertor for reducing $NO_x$ to NO; a sample gas supply passage on the downstream side of the $NO_x$ convertor through which the sample gas flows to the NO detector being provided with a first capillary therein; an overflow passage connecting with the sample gas supply passage between the $NO_x$ convertor and the first capillary and having a second capillary therein; and a diluent air supply passage connecting with the sample gas supply passage downstream of the first capillary and upstream of the NO detector; the diluent air supply passage having a third capillary therein; and a heating zone for the $NO_x$ convertor including at least the connections of the first capillary, the overflow passage, and the diluent air supply passage with the sample gas supply passage.

Additionally, the second capillary, and/or the third capillary may also be included within the heating zone of the analyzer.

Similarly, the $NO_x$ convertor may also be included within the heating zone of the analyzer.

Since the first capillary provided in the sample gas supply passage and the second capillary provided in the overflow passage are arranged within the heating zone of the $NO_x$ convertor, both the first capillary and the second capillary can be prevented from clogging with solidified substances, such as solidified phthalic acid anhydride. As a result, an appointed or design flow rate of sample gas can be distributed toward the NO detector. Also, the vapor pressures prevailing within these capillaries also can be sufficiently lowered so as to prevent them from being clogged by solidified materials at normal temperatures. This is true even if substances such as phthalic acid anhydride, apt to solidify at normal temperatures, as explained above, exists in the sample gas flow, because the sample gas is diluted with a diluent air within the heating zone. The result is that the sample gas containing no solidified substances can be introduced into the NO detector.

In addition, even if the sample gas which has passed through the first capillary is diluted with the diluent air, the same flow rate of the sample gas is introduced into the NO detector. In short, the same number of NO molecules per unit time is introduced into the NO detector, and the response of this detector is not changed by the addition of the diluent air. Accordingly, there is no need to worry about a lowering in accuracy of detection due to addition of the diluent air to the sample gas flow to the NO detector.

BRIEF DESCRIPTION OF THE DRAWING

The drawing is a schematic flow circuit diagram showing one preferred embodiment of an $NO_x$ analyzer according to the present invention.

DETAILED DESCRIPTION OF THE PREFERRED EMBODIMENTS

The preferred embodiments of the present invention will be described below in detail with reference to the drawing.

The drawing shows a construction of principal parts of an $NO_x$ analyzer 1. Referring to the drawing, reference numeral 2 designates an $NO_x$ convertor for reducing $NO_x$ in a sample gas to NO. Reference numeral 3 designates a heating zone heated and controlled in humidity by means of a heating device (not shown). Within the heating zone 3 the temperature in the $NO_x$ convertor 2 is set at about 220° C.

The $NO_x$ convertor 2 is provided with an upstream sample gas supply passage 4a for supplying to the convertor 2 the sample gas connected to passage 4a at an inlet thereof. A downstream sample gas supply passage 4b connected with an outlet of the convertor 2 is provided with a first capillary 5 therein. This sample gas supply passage 4b between first capillary 5 and the NO$_x$ convertor 2 is also provided with an overflow passage 7 leading to the ambient atmosphere. Overflow passage 7 has a second capillary 6 therein. In other words, the second capillary 6 is branch connected with the downstream sample gas supply passage 4b.

Preferably, a flow rate of the sample gas is set generally at about 200 to 240 cc/min in the NO$_x$ convertor 2, at about 40 to 50 cc/min in the first capillary 5, and at about 170 to 200 cc/min in the second capillary 6, respectively. That is, the sample gas flow rate through the first capillary of 40 to 50 cc/min, plus the 170 to 200 cc/min in the second capillary results in a volume flow rate of about 210 to 250 cc/min through the convertor 2. It will be noted that these are volume flow rates, not mass flow rates, so that the numbers are merely approximations, and need not add to the same total.

On the other hand, the sample gas supply passage 4b is provided with a diluent air passage (diluent air supply passage) 9 having a third capillary 8 therein. In other words, the diluent air passage 9 is also branch connected with the sample supply passage 4b, and is disposed on the downstream side of the first capillary 5 so as to add clean air to the sample gas at a flow rate of 500 cc/min. That is to say, the sample gas flow through the first capillary is diluted about 10 times with clean air before being introduced into an NO detector 11 through a filter 10.

The confluence 9a of the sample gas flow through the first capillary 5 with the diluent air flow through passage 9, the second capillary 6 itself, and the third capillary 8 itself, as shown in the drawing, and controlled in humidity at about 220° C., as above described. The convertor 2 is also arrange within the heating zone 2, as shown.

With the NO$_x$ analyzer 1 having such a construction as is schematically depicted in the drawing, even in the cases where aromatic hydrocarbons such as xylene, are contained in the sample gas, the deposition of solid substances on the outlet side of the NO$_x$ convertor 2 is reduced. Accordingly, the maintenance operations required by the analyzer are also reduced; and a highly reliable analytical value can be obtained from the analyzer.

In more detail, since the first capillary 5 provided in the sample gas supply passage 4a, and the second capillary 6 provided in the overflow passage 7, are both arranged within the heating zone 3, both the first capillary and the second capillary can be prevented from clogging with solidified substances. It follows that appointed, or design, flow rate of sample gas can be reliably distributed or flowed toward the NO detector 11.

Further, since the sample gas which has passed through the first capillary 5 is diluted with a diluent air within the heating zone 3, and this diluent air is heated by its passage through the supply passage 9 and the third capillary 8, even if substances which are apt to solidify at normal temperatures, such as phthalic acid anhydride, exist in the sample gas flow, their vapor pressures can be sufficiently lowered and thus they can be prevented for a time from being solidified outside of the heating zone 3 even where the remainder of the apparatus is at more normal temperatures. The result is that the sample gas containing no solidified substances can be introduced into the NO detector 11 through the filter 10. The dilution of the sample gas by as much as ten times as much clean heated diluent air is effective to accomplish this delay in the solidification of the substances which might otherwise quickly solidify and plug the filter 10 or analyzer 11.

Thus, the diluted sample gas containing the appointed quantity of sample gas, in which NO$_x$ has been reduced to NO, is introduced into the NO detector 11. The detector 11 is capable of obtaining the desired highly reliable analytical value for the amount of NO in the sample gas. And the delay of solidification of the solid materials in the sample gas remarkably reduces the clogging of the filter 10. This filter 10 is still effective for removing the solidified substances which are present in the sample gas flow. However, the filter 10 is not called upon to capture nearly so much solid as would otherwise be the case, remarkably saving labor and time required for cleaning, exchanging, and the like of the filter 10. Thus, idle time and operating costs for the analyzer 1 are greatly reduced.

In addition, even though the sample gas which has passed through the first capillary 5 is diluted with the diluent air from passage 9, the flow of the sample gas introduced into the NO detector 11 contains no fewer molecules of NO. In short, a number of NO molecules per unit time is not changed by the addition of the diluent air, and there is no lowering in accuracy of detection due to this air dilution of the sample gas.

Furthermore, it is not always required that the third capillary 8 provided in the diluent air passage 9 be arranged within the heating zone 3; that is, it is sufficient that the confluence 9a of the sample gas flow and the diluent air flow be arranged within the heating zone 3.

As above described, according to the present invention, the sample gas supply passage 4 on the downstream side of the NO$_x$ convertor 2 is provided with the first capillary 5 therein; the sample gas supply passage between the first capillary 5 and the NO$_x$ convertor 2 is provided with the overflow passage 7 having the second capillary 6 branch connected therewith; the sample gas supply passage 4 on the downstream side 4b of the first capillary 5 is provided with the diluent air supply passage 9 having the third capillary 8 therein branch connected to the supply passage 4b; and at least the confluence 9a of the first capillary 5 and the diluent air supply passage 9 with the sample gas supply passage 4b, and the second capillary itself are arranged within the heating zone 3 of the NO$_x$ convertor. The diluted sample gas still containing the appointed quantity of sample gas along with the diluting clean air, and in which NO$_x$ has been reduced to NO, is introduced into the NO detector 11 to result in the obtaining of a highly reliable analytical value for the amount of NO$_x$ in the sample gas, and remarkably reducing the clogging of the filter 10 for removing the solidified substances. The result is a remarkable saving in both labor and time required for cleaning, exchanging, and the like of the filter 10, reducing idle time and operation cost.

What is claimed is:

1. An analyzer constructed so to introduce a sample gas into an NO detector through an NO$_x$ convertor comprising:
   a sample gas inlet line leading into an NO$_x$ convertor for reducing NO$_x$ to NO;
   a sample gas supply passage on the downstream side of said NO$_x$ convertor through which said sample gas flows to said NO detector being provided with a first capillary therein;
   an overflow passage leading to ambient atmosphere and connecting with said sample gas supply passage between said $NO_x$ convertor and said first capillary and having a second capillary therein;

a diluent air supply passage connecting with said sample gas supply passage downstream of said first capillary and upstream of said NO detector, said diluent air supply passage having a third capillary therein; and a heating zone for the $NO_x$ convertor including at least the connections of the first capillary, the overflow passage, and the diluent air supply passage with said sample gas supply passage.

2. The analyzer of claim 1 wherein additionally said second capillary is disposed within said heating zone.

3. The analyzer of claim 1 wherein additionally said third capillary is also included within said heating zone of the analyzer.

4. The analyzer of claim 1 wherein said $NO_x$ convertor is also included within the heating zone of the analyzer.

5. The analyzer of claim 1 wherein said $NO_x$ convertor is included in said heating zone along with said first and second capillaries.

6. The analyzer of claim 5 wherein said third capillary is included in said heating zone.

7. A method of quantitatively analyzing a sample gas flow for $NO_x$, said method including the steps of;

reducing in a convertor the $NO_x$ in the sample gas flow to NO;

flowing a first portion of the reduced sample gas flow through a first capillary to an analysis cell;

flowing a second portion of the reduced sample gas flow through a second capillary to ambient atmosphere;

including said first and said second capillaries in a heating zone; and diluting said first sample gas portion with air after flowing of said first sample gas portion through said first capillary and before flowing of said first sample gas portion to said analysis cell.

8. The method of claim 7 additionally including the step of flowing said air through a third capillary before introducing said air into said first sample gas portion.

9. A sample gas analyzer comprising:

a sample gas inlet supply line within which a sample gas including $NO_x$ flows to;

a convertor reducing the $NO_x$ in the sample gas into NO, the reduced sample gas flowing from the convertor via a sample gas outlet supply line to;

a first capillary communicating a first flow portion of said reduced sample gas to;

a filter communicating said first flow portion of said reduced sample gas to;

an analysis cell;

said analyzer further including a second capillary branch connected with said sample gas outlet supply line and communicating a second flow portion of said reduced sample gas to ambient atmosphere;

a heating zone including at least said convertor and said first and said second capillaries; and a diluent air supply line including a third capillary and branch connecting a flow of diluent air into said first flow portion of reduced sample gas intermediate of said first capillary and said filter.

10. The analyzer of claim 9 additionally including within said heating zone said branch connection of said flow of diluent air into said first flow portion of reduced sample gas.

11. The analyzer of claim 10 additionally including within said heating zone said third capillary.

12. The analyzer of claim 11 wherein said filter and said analysis cell are located outside of said heating zone.

13. The analyzer of claim 9 wherein said first capillary, said second capillary, and said third capillary are all within said heating zone.

14. A sample gas analyzer comprising:

a filter communicating with a downstream gas analysis cell;

a sample gas supply passage leading to a convertor;

a heating zone;

and within said heating zone:

said convertor for reducing $NO_x$ in a sample gas to NO; and a branched flow path leading reduced flow of sample gas from said convertor, said branched flow path including a first branch of said flow path leading through a first capillary and then outwardly of said heating zone to flow a first portion of said reduced sample gas to said filter and gas analysis cell, a second branch of said flow path leading through a second capillary and then outwardly of said heating zone to flow a second portion of said reduced sample gas to ambient atmosphere, and a third branch of said flow path leading inwardly from outside of said heating zone to conduct a flow of diluent air through a third capillary within said heating zone to said filter and analysis cell, said second branch connecting with said first branch at a position between said first capillary and said convertor, said first and said third branches of said flow path joining downstream of said first capillary for confluence of said first portion of reduced sample gas and said flow of diluent air prior to flowing together to said analysis cell.

* * * * *